US008073101B2

(12) United States Patent
Massie et al.

(10) Patent No.: US 8,073,101 B2
(45) Date of Patent: Dec. 6, 2011

(54) DIGITAL MODALITY MODELING FOR MEDICAL AND DENTAL APPLICATIONS

(76) Inventors: Ronald E. Massie, Lake Ozark, MO (US); Christopher J Leslie, Camdenton, MO (US)

( * ) Notice: Subject to any disclaimer, the term of this patent is extended or adjusted under 35 U.S.C. 154(b) by 856 days.

(21) Appl. No.: 11/932,809

(22) Filed: Oct. 31, 2007

(65) Prior Publication Data
US 2008/0051650 A1   Feb. 28, 2008

Related U.S. Application Data

(63) Continuation-in-part of application No. 11/224,472, filed on Sep. 12, 2005, which is a continuation of application No. 10/351,567, filed on Jan. 24, 2003, now Pat. No. 6,944,262, which is a continuation-in-part of application No. 10/134,153, filed on Apr. 27, 2002, now abandoned, which is a continuation of application No. 09/452,348, filed on Dec. 1, 1999, now Pat. No. 6,381,301.

(51) Int. Cl.
*G01B 15/00* (2006.01)
(52) U.S. Cl. .......................................... 378/54; 378/191
(58) Field of Classification Search .............. 378/38–39, 378/168, 191, 189, 54–55
See application file for complete search history.

(56) References Cited

U.S. PATENT DOCUMENTS

| | | | |
|---|---|---|---|
| 3,949,229 A | 4/1976 | Albert | |
| 4,104,532 A | 8/1978 | Weiss | |
| 4,188,537 A | 2/1980 | Franke | |
| 4,239,971 A | 12/1980 | Cushman | |
| 4,259,853 A | 4/1981 | Fleissner | |
| 4,628,356 A | 12/1986 | Spillman | |
| 4,783,793 A | 11/1988 | Virta et al. | |
| 4,813,060 A | 3/1989 | Heubeck et al. | |
| 4,823,369 A | 4/1989 | Guenther et al. | |
| 4,856,038 A | 8/1989 | Guenther et al. | |
| 4,941,164 A | 7/1990 | Schuller et al. | |

(Continued)

FOREIGN PATENT DOCUMENTS

CA   2390334   11/2008
(Continued)

OTHER PUBLICATIONS

"Notice of Reason for Rejection", Japan Patent Application No. 2001-541403 based on PCT/US00/32905, (Nov. 24, 2009).

(Continued)

*Primary Examiner* — Hoon Song
(74) *Attorney, Agent, or Firm* — Law Office of Mark Brown LLC; Mark E. Brown

(57) ABSTRACT

A digital modality modeling system includes a computer with a digital memory adapted for storing patient densitometry information, an input and an output. An input subsystem includes a pair of source/receptor units mounted on a signal positioning subsystem, which is adapted for moving the source/receptor units through predetermined paths of movement, which can be circular or linear. The resulting tomographic data is synthesized to form any 3-D model or image, which is output for further analysis. A digital tomosynthesis method includes the steps of moving a pair of sensor/receptor units relative to a patient. The resulting signals output by the receptor are digitized and synthesized to form a 3-D image or model. Multiple depths of penetration and multiple widths can be captured from single acquisitions using digital tomosynthesis signal processing techniques.

12 Claims, 19 Drawing Sheets

U.S. PATENT DOCUMENTS

| | | | |
|---|---|---|---|
| 5,093,852 A | 3/1992 | Nishikawa et al. | |
| 5,195,114 A | 3/1993 | Sairenji et al. | |
| 5,214,686 A | 5/1993 | Webber | |
| 5,306,306 A | 4/1994 | Bisek et al. | |
| 5,335,260 A | 8/1994 | Arnold | |
| 5,480,439 A | 1/1996 | Bisek et al. | |
| 5,503,559 A | 4/1996 | Vari | |
| 5,528,645 A | 6/1996 | Koivisto | |
| 5,533,080 A | 7/1996 | Pelc | |
| 5,579,361 A | 11/1996 | Augais et al. | |
| RE35,423 E | 1/1997 | Adams et al. | |
| 5,677,940 A | 10/1997 | Suzuki et al. | |
| 5,784,429 A | 7/1998 | Arai | |
| 5,785,041 A | 7/1998 | Weinstein et al. | |
| 5,793,837 A | 8/1998 | Mezhinsky et al. | |
| 5,828,720 A | 10/1998 | Syrjanen | |
| 5,828,721 A | 10/1998 | Schulze-Ganzlin et al. | |
| 5,828,722 A | 10/1998 | Ploetz et al. | |
| 5,835,555 A | 11/1998 | Barry et al. | |
| 5,836,876 A | 11/1998 | Dimarogonas | |
| 5,838,765 A | 11/1998 | Gershman | |
| RE36,162 E | 3/1999 | Bisek et al. | |
| 5,917,882 A | 6/1999 | Khutoryansky et al. | |
| 5,917,883 A | 6/1999 | Khutoryansky et al. | |
| 5,930,327 A | 7/1999 | Lin | |
| 5,995,583 A | 11/1999 | Schick et al. | |
| 6,038,287 A | 3/2000 | Miles | |
| 6,069,935 A | 5/2000 | Schick et al. | |
| 6,381,301 B1 | 4/2002 | Massie | |
| 6,385,283 B1 | 5/2002 | Stein et al. | |
| 6,405,071 B1 | 6/2002 | Analoui | |
| 6,424,694 B1 | 7/2002 | Molteni | |
| 6,496,558 B2 | 12/2002 | Graumann | |
| 6,664,986 B1 | 12/2003 | Kopelman et al. | |
| 6,690,761 B2 | 2/2004 | Lang et al. | |
| 6,821,116 B2 | 11/2004 | Severance | |
| 7,099,428 B2 | 8/2006 | Clinthorne et al. | |
| 7,203,273 B2 | 4/2007 | Linnosaari | |
| 2002/0114425 A1 | 8/2002 | Lang et al. | |
| 2002/0178032 A1 | 11/2002 | Benn et al. | |
| 2006/0067464 A1* | 3/2006 | Clinthorne et al. | 378/38 |

FOREIGN PATENT DOCUMENTS

| | | |
|---|---|---|
| EP | 0180482 | 5/1986 |
| EP | 0314506 | 5/1989 |
| EP | 0652433 | 5/1995 |
| EP | 1237483 | 11/2008 |
| WO | WO9311707 | 6/1993 |
| WO | WO-0138824 | 5/2001 |
| WO | WO 01/39667 | 6/2001 |

OTHER PUBLICATIONS

Krennmair, Gerald, MD et al., "Maxillary Sinus Aspergillosis: Diagnosis and Differentiation of the Pathogenesis based on Computed Tomography Densitometry of Sinus Concretions", American Association of Oral and Maxillofacial Surgeons,(1995),657-663.

Elsasser, Urs, Ph.D., et al., "Bone Density Measurement with Computed Tomography", *British Medical Bulletin* vol. 36, No. 3, (1980), 293-296.

Exner, G., M.D., et al., "Bone Densitometry Using Computed Tomography", *British Journal of Radiology*, vol. 52, (1979), 14-23.

"Notice of Reason for Rejection", Japan Patent Application No. 2006-502953 based on PCT/US2004/001825, (Aug. 3, 2009).

Boyde, A. et al., "The Mineralization Density of Iliac Crest Bone From Children with Osteogenesis Imperfecta", A. Boyde, R. Travers, F.H. Glorieux, S. J. Jones, *The Mineralization Density of Iliac Crest Bone From Children with Osteogenesis Imperfecta, Calcified Tissue International*, vol. 64 Issue 3, Mar. 1999, p. 185-190.

Branemark, M.D., Ph.D., Ingvar et al., "Tissue-Integrated Prosthese, Osseointegration in clinical denistry", *Quintessence Publishing Co., Inc.*, 1985, 11-70.

"International Search Report", PCT/US00/32905, (Jan. 26, 2001).

"Written Opinion of the ISA", PCT/US/04/01825, Feb. 25, 2005.

"Supplement European Search Report", Massie Application No. 04704878.0, PCT/US2004001825, Jun. 10, 2008.

"Notice of Reason for Rejection", Japan Appl. No. 2001-541403 corresponding to PCT/US00/32905, 2001.

"Final Decision for Rejection", Japan Patent Application No. 2006-502953 based on PCT/US2004/001825, 2006.

* cited by examiner

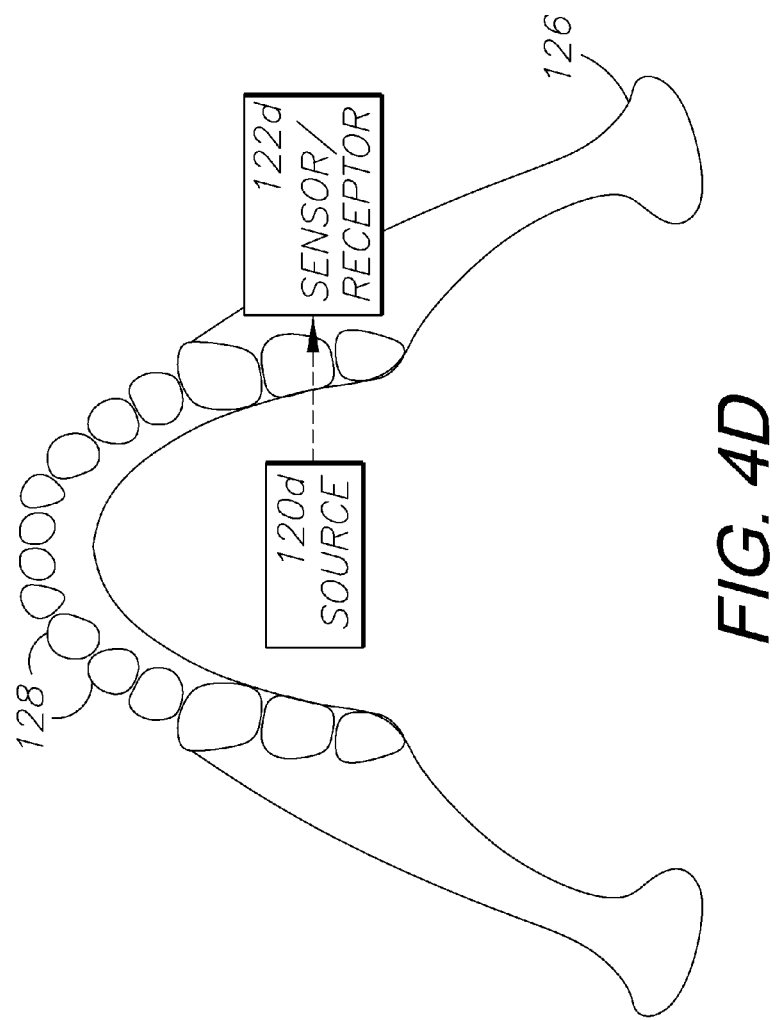

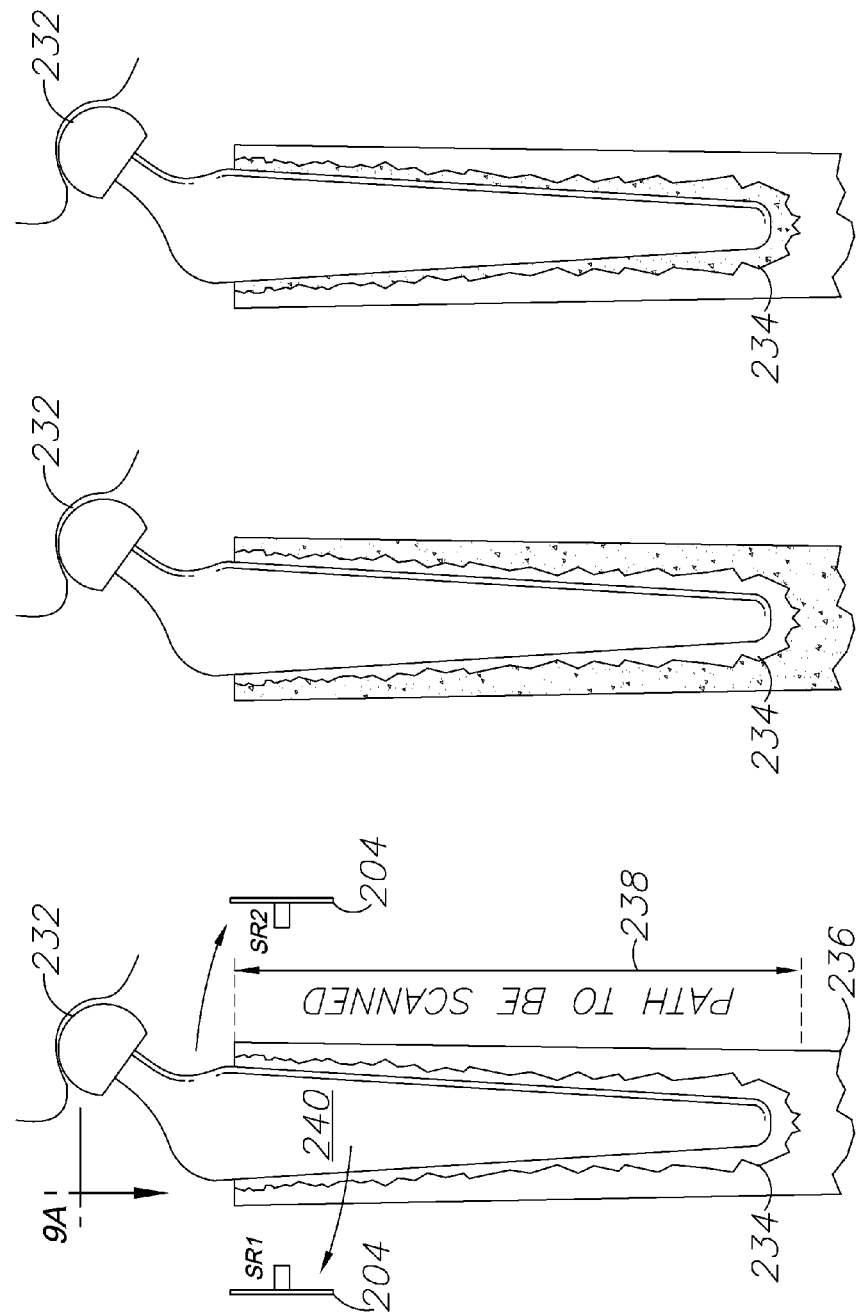

DIGITAL MODALITY MODELING FOR MEDICAL AND DENTAL APPLICATIONS

CROSS-REFERENCE TO RELATED APPLICATIONS

This application is a continuation-in-part of Ser. No. 11/224,472 filed Sep. 12, 2005. which is a continuation of Ser. No. 10/351,567 filed Jan. 24, 2003, now U.S. Pat. No. 6,944,262, which is a continuation-in-part of Ser. No. 10/134,153, filed Apr. 27, 2002, now abandoned, which is a continuation of Ser. No. 09/452,348, filed Dec. 1, 1999, now U.S. Pat. No. 6,381,301, in which priority is claimed and which are incorporated herein by reference.

BACKGROUND OF THE INVENTION

1. Field of the Invention

The present invention relates generally to digital modality modeling, such as tomosynthesis, and in particular to dental and orthopedic diagnosis, forensics, identification, biometrics and treatment applications of a densitometry modeling system and method.

2. Description of the Related Art

The field of dental diagnostics is generally concerned with locating pathologies in the dental structure, i.e. the teeth and the surrounding tissue and bone. Some of the more common pathologies are: 1) caries associated with decay; 2) fractures; 3) apical abscesses, and 4) morphologies of pulpal chambers and canals. The system and method of the present invention are primarily, but not exclusively, concerned with detecting these pathologies and with orthopedics.

Early detection of dental pathologies is very important in minimizing damage. Conventional diagnosis procedures are generally performed using dental X-rays (both fixed beam and scanning beam), explorers, and other conventional equipment.

Incipient caries, particularly those located within the enamel surface, often go undetected with conventional equipment. When such caries are finally found, considerable damage to tooth structure may have already occurred. Subsurface, incipient caries are located entirely within the enamel layer of the teeth. They are particularly difficult to locate using conventional diagnostic equipment and procedures. By the time such incipient caries are located, the extent of the damage is often 17% to 23% greater than it would appear to be on a conventional X-ray negative.

Dental fractures can result from bruxism (teeth grinding), trauma, etc. The dental structure that has been weakened by various causes, such as decalcification, is particularly susceptible to fractures. Fractures can assume various configurations, including "craze", vertical, oblique and horizontal line patterns. Fracture patterns and configurations can be particularly difficult to locate using conventional X-ray equipment and procedures. For example, fractures which are generally parallel to the X-ray beam are often undetectable on an X-ray negative. Undetected, and hence untreated, fractures can provide direct paths through the enamel layer of the teeth whereby bacteria can invade the dentin and pulp layers. Pathologies in the dentin and pulp layers are often associated with considerable pain and tooth loss.

Apical abscesses comprise yet another dental condition which can be difficult to diagnose with conventional equipment, particularly in the early stages. Advanced apical abscesses can cause considerable pain because they involve the neurovascular bundles located in the root canals as well as the osseous tissue around the apex of the root. Early detection of apical abscesses can lead to appropriate, early-stage treatment, thus avoiding advanced disease processes with resultant pain, swelling, and other serious health consequences and complications.

Tomography or sectional radiography techniques using scanning X-ray beams have previously been employed for dental applications. For example, U.S. Pat. Nos. 4,188,537; 4,259,583; 4,823,369; 4,856,038; and 5,214,686 all relate to dental X-ray diagnosis utilizing scanning techniques and are incorporated herein by reference.

In the medical field, densitometry procedures are used for measuring bone morphology density (BMD) by utilizing scanning X-ray beam techniques. Examples are shown in U.S. Pat. Nos. 5,533,080; 5,838,765; and U.S. Pat. No. Re. 36,162, which are incorporated herein by reference. Medical applications of densitometry include the diagnosis and treatment of such bone diseases as osteoporosis. Dual energy x-ray absorptiometry (DEXA) utilizes x-rays with different peak energy levels for distinguishing soft and hard (e.g., muscle and skeletal) tissue structures based on their absorption of the x-rays at different energy levels.

The availability of relatively fast computers with large memories at reasonable costs has led to the digitalization of X-ray images for mapping BMD models in various formats. For example, BMD images use color to identify varying densities. Digital BMD patient models are also used for comparison purposes with standard models and with patients' own prior BMD histories. Age correction factors can be applied to patients' models for diagnosing and monitoring the onset and progress of such medical conditions as osteoporosis and the like. The present invention utilizes such densitometry modeling and mapping techniques for dental applications.

In addition to pathology detection and diagnosis, the present invention has applications in monitoring osseointegration, which occurs at the interface between bone structures and prostheses, such as implants and replacement joints. For example, dental implants osseointegrate with patients' dental structure. The application of tomographical densitometry techniques to osseointegration monitoring can provide the dental or medical practitioner with important information in evaluating the effectiveness of implant procedures.

Digital tomosynthesis utilizes computers for digitizing tomographic densitometry data and constricting 3-D models of patient and prosthetic regions of interest (ROIs). Using digital tomosynthesis techniques, partial rotation of source/receptor units and relatively few discrete exposures can produce sufficient information to construct 3-D models. By digitally processing the resulting images, tomographic slices at different depths and with different thicknesses can be reconstructed from individual data acquisitions, thus minimizing radiation exposure and procedure time. Digital tomosynthesis techniques have been utilized in mammography applications. The resulting 3-D digital tomosynthesis models are utilized for diagnostic, treatment, forensic and related purposes.

Other modeling and imaging modalities include computerized tomography (CT), magnetic resonance imaging (MRI), ultrasound, sonar, Doppler effect, photon emission tomography (PET) and single photon emission computed tomography (SPECT) scanning. The present invention is adapted for medical and dental applications involving the acquisition of signals, which are digitized and further processed to produce 3-D models corresponding to patient regions of interest (ROIs) including both hard and soft tissue structures and prosthetics.

Heretofore there has not been available a system or method for applying digital tomosynthesis and related modalities to dental and medical applications such as the detection of caries and decalcification and the monitoring of osseointegration in connection with dental and medical prostheses, with the advantages and features of the present invention.

SUMMARY OF THE INVENTION

In the practice of an aspect of the present invention, a digital tomosynthesis, or related modality, system and method are provided for dental and orthopedic densitometry modeling. The system utilizes a controller (computer) with a microprocessor and a digital memory device. An input device inputs data to the microprocessor for controlling the operation of the modeling system and for providing a database including densitometry parameters for comparison with a patient's densitometry model. The controller controls the operation of X-ray equipment, which is adapted for scanning patients' dental and orthopedic structures along preprogrammed scan paths. The X-ray output is processed by the microprocessor for creating a densitometry model, which can be output in various formats. In the practice of the method of the present invention, a patient and the X-ray equipment are positioned relative to each other. A controller is preprogrammed with a scan path and with data corresponding to the patient. The X-ray equipment emits and detects X-ray beams at first and second energy levels to provide densitometry output. The densitometry output is digitized and merged to provide a tomographic model, which can be compared to predetermined parameters unique to the patient. The model can be output in various formats, including a visual image color-coded to depict varying dental and orthopedic structure densities. Applications of the system and methodology include diagnosis, treatment, identification, forensics and biometrics. Digital tomosynthesis techniques can also be utilized with the present invention, and include both dental and orthopedic applications. Combined source and receptor units can be rotated or moved axially around and along multiple axes to capture data for synthesizing by the computer, which provides output in the form of 3-D images and models.

The drawings constitute a part of this specification and include exemplary embodiments of the present invention and illustrate various objects and features thereof.

BRIEF DESCRIPTION OF THE DRAWINGS

FIG. 4d is a diagram of an application with an internal beam source and an internal sensor/receptor.

FIG. 10 shows an application of the invention in connection with a hip prostheses.

FIG. 11 shows an application of the invention in connection with the hip prostheses, with a filtering technique for particularly displaying bone material.

FIG. 12 shows an application of the invention in connection with the hip prosthesis, with a filtering technique for particularly displaying an interface between the bone and the prosthesis.

DETAILED DESCRIPTION OF THE PREFERRED EMBODIMENTS

I. Introduction and Environment

Figure 1:
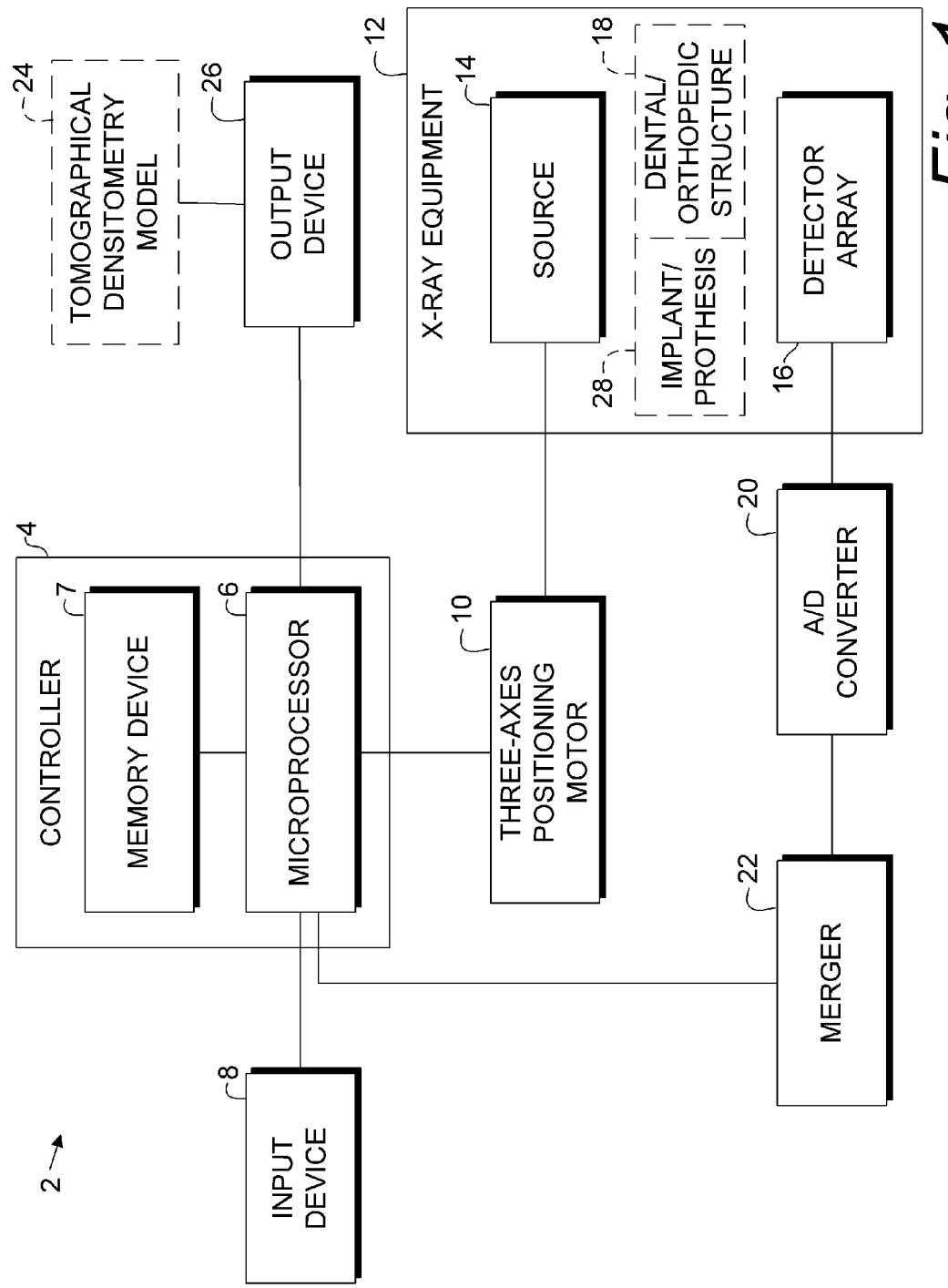
FIG. 1 is a schematic, block diagram of a dental and orthopedic densitometry modeling system embodying the present invention.

As required, detailed embodiments of the present invention are disclosed herein: however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. "Modeling" is used broadly herein to cover capturing, converting, creating, analyzing and storing patient information, such as densitometry, using various modalities for a variety of applications such as imaging, diagnostics, forensics, etc. Examples discussed herein are not to be interpreted as limiting.

II. Dental Densitometry Modeling System 2

Referring to the drawings in more detail, the reference numeral 2 generally designates a dental and orthopedic densitometry modeling system embodying the present invention. The system 2 includes a controller 4 with a microprocessor 6 connected to a digital memory device 7. The hardware components of the controller 4, i.e. the microprocessor 6 and the memory device 7, can comprise any of a number of suitable hardware devices which are commercially available and are suitable for this application. In addition to various programmable logic devices (PLDs) and special-purpose microprocessors, general purpose, commercially available personal computers can be utilized in the controller 4. The controller 4 can be programmed in any suitable manner utilizing any of a variety of commercially available programming languages and software development systems.

The microprocessor 6 is adapted to receive input from one or more input devices 8, such as a keyboard, a pointing device (e.g., a mouse), a communications link, or another computer. Without limitation on the generality of useful data which can be input via the input device(s) 8, such data can include: 1) a patient's dental and orthopedic records, including previous tomographical densitometry models; 2) baseline tomographical densitometry models, which can be adjusted to accommodate for such factors as age, gender, size, weight, etc.; and 3) a preprogrammed scan path for the X-ray equipment.

The microprocessor 6 controls a positioning motor 10 which is operably connected to X-ray equipment 12 and is adapted for moving same through three axes of movement. Examples of X-ray equipment adaptable for use with the present invention are disclosed in U.S. Pat. Nos. 5,533,080; 5,838,765; and U.S. Pat. No. Re. 36,162, which are incorporated herein by reference. The X-ray equipment 12 includes an X-ray beam source 14 and a detector array 16. The X-ray beam can suitably collimated to assume any suitable configuration, such as fan, pencil, cone, etc. With the scanning technique disclosed, a restricted (i.e. collimated) beam is preferred. The source and the detector array 14, 16 are adapted for positioning on either side of a patient's dental/orthopedic structure 18.

Analog signals from the detector array 16 are output to an analog-to-digital (A/D) convertor 20, from which digitized signals are transmitted to a merger device 22 for merging into formats suitable for processing and analyzing by the microprocessor 6. The microprocessor 6, using data from the merger device 22, creates a tomographical densitometry model 24 which is transmitted to an output device or devices 26. Without limitation on the generality of useful output devices 26, it can comprise a monitor, a display, a printer, a communications link, and/or another computer. For example, a color printer can be utilized to provide a color-coded graphical representation of the tomographical densitometry model 24. The color coding can correspond to densities, thus identifying potential problem areas where decalcification has occurred and resulted in lower density. The tomographical densitometry model 24 can also be useful for monitoring osseointegration, since the density of the dental/orthopedic structure 18 (tissue and bone) in the vicinity of an implant 28 or other prostheses can provide an important diagnostic tool for the use of the dental or medical practitioner in assessing the effectiveness of an implant or prosthetic procedure. The tomographical densitometry model 24 is also entered into the computer's memory device 7.

III. Dental and Orthopedic Densitometry Modeling Method

Figure 2:
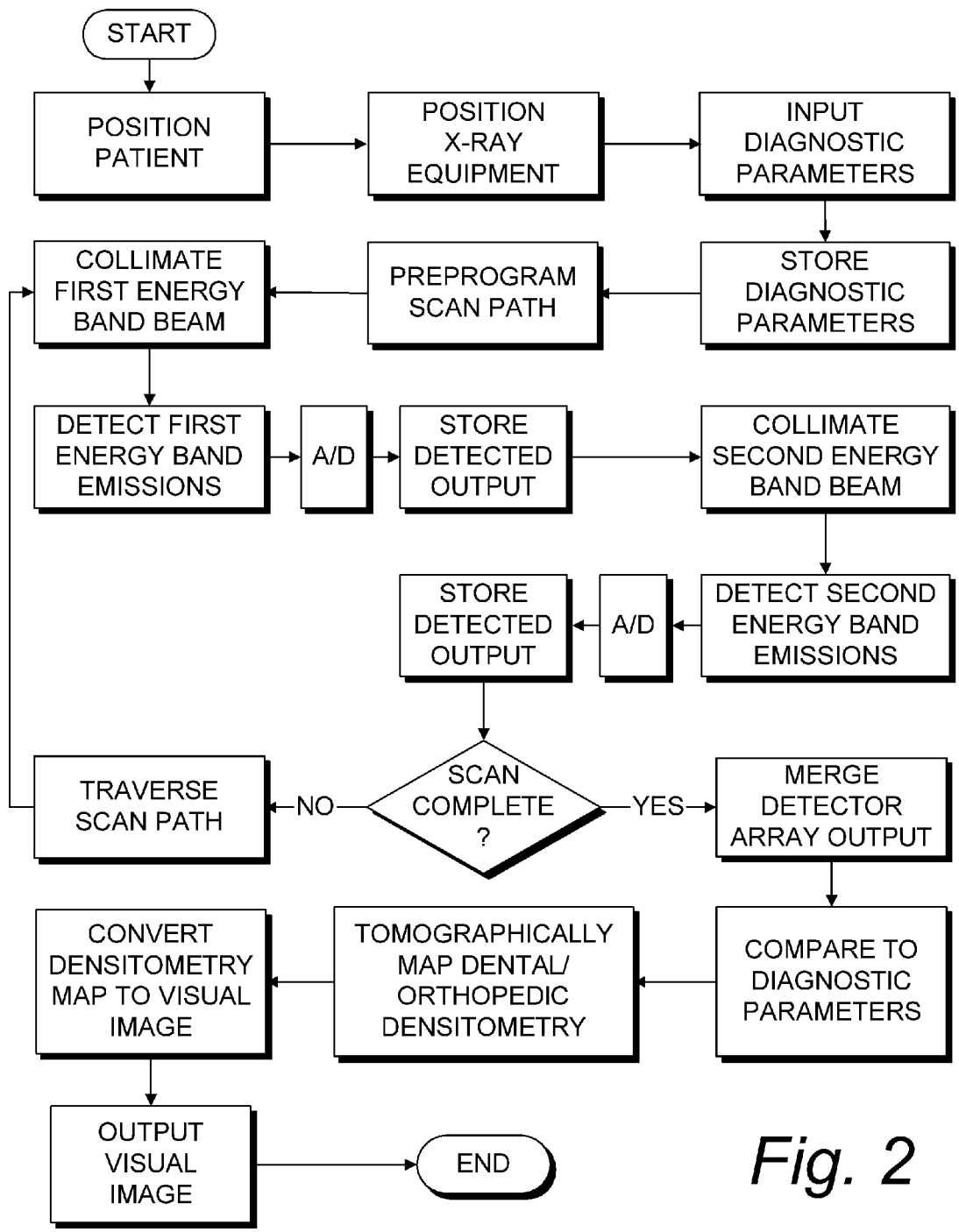
FIG. 2 is a flowchart of a dental and orthopedic densitometry modeling method embodying the present invention.

FIG. 2 is a flow chart of a dental and orthopedic densitometry method embodying the present invention. The method steps include positioning a patient and positioning the X-ray equipment relative to the patient, i.e. with the patient's dental/orthopedic structure to be examined located between the X-ray source 14 and the detector array 16.

Diagnostic parameters are input to the system and can comprise, for example, the patient's prior tomographical densitometry models and standardized models. The tomographical densitometry models can be corrected and/or adjusted to account for patients' age, gender, physical characteristics, etc. The input diagnostic parameters can be stored in the computer's memory device. A scan path for the X-ray equipment is preprogrammed in the computer.

The scanning procedure is commenced by collimating a first energy band beam, detecting emissions from same with a detector array, and converting the analog output of the detector array to a digital signal. The digital signal is output for storage in the computer. The steps of collimating the energy band beam and detecting, digitizing and storing same are repeated for a second energy band beam. The Bisek et al. U.S. Pat. No. Re. 36,362 discloses the use of dual-energy X-ray beams in medical densitometry applications. As discussed therein, dual-energy densitometry can result in a more accurate patient model.

The X-ray equipment then traverses the preprogrammed scan path and the first/second energy band steps are repeated until the scanning procedure is complete. The digitized detector array output is merged and compared to the diagnostic parameters which are stored in the computer's memory. The dental/orthopedic densitometry is tomographically modeled and output, for example to a monitor or printer for converting the model to a visual image. The visual image is output in a visible form for use by dental and medical practitioners.

IV. Modified Embodiment Densitometry Modeling Systems 102

Figure 3:
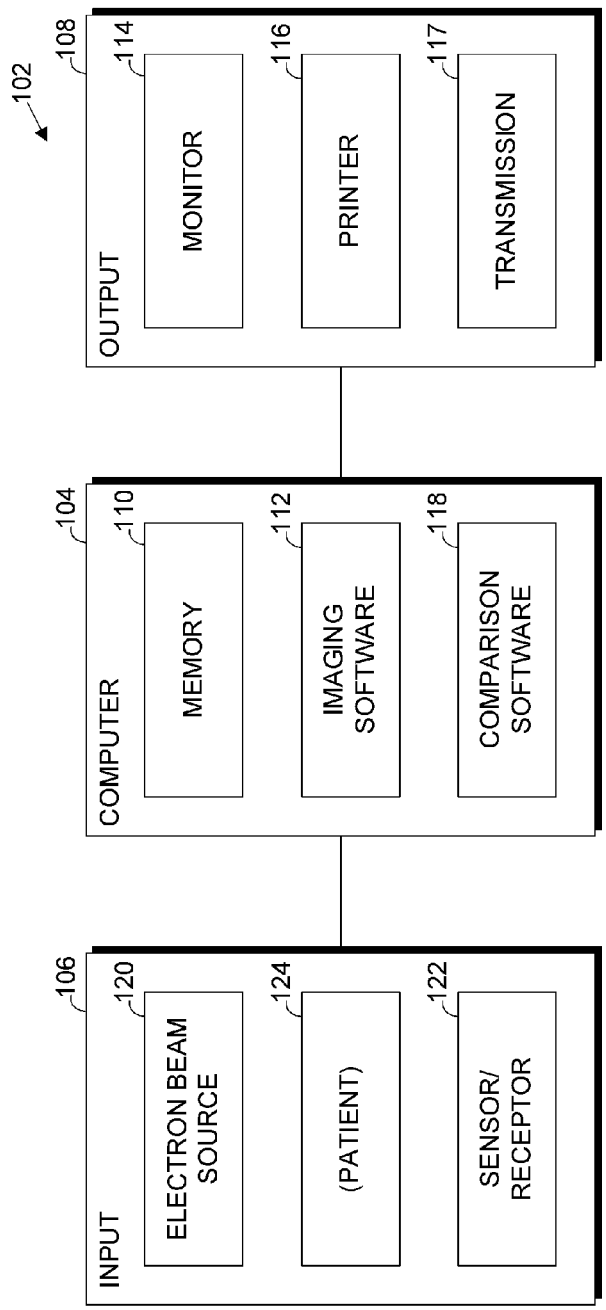
FIG. 3 is a block diagram of a dental or orthopedic densitometry modeling system comprising a first modified embodiment of the present invention.

A densitometry modeling system 102 comprising a first modified embodiment of present invention is shown in FIG. 3 and generally includes a computer 104 with an input 104a and an output 104b. Input and output devices 106 and 108 are connected to the computer input and output 104a,b respectively.

The computer 104 includes a memory 110, such as a hard drive, a tape drive, an integrated circuit (e.g., RAM) or some other suitable digital memory component, which can be either internal or external to the computer 104. Imaging software 112 is provided for converting the digital data into images, which are adapted for visual inspection by displaying same on a monitor 114 or by printing same on a printer 116 of the output device 108. Such images can also be transmitted by a suitable transmission device 117, such as a fax or modem. The computer 104 also includes comparison software 118, which is adapted for digitally comparing baseline and patient-specific dental and orthopedic densitometry models.

The input device 106 includes a beam source 120 and a sensor/receptor 122, which are adapted for positioning with at least a portion of the patient 124 therebetween. A wide variety of source and sensor/receptor combinations are included in the scope of the present invention. Preferably the beam source 120 emits a collimated beam adapted for scanning the patient's dental/orthopedic structure. Such devices can be located internal or external to the patient and include "wands" and "pens". Micro devices are also available that are adapted for mounting on the end of a stylus apparatus. Both hard-wired and wireless (RF) types of source devices can be employed. External devices include beam heads mounted on articulated arm assemblies, which are commonly found in dental operatories and other medical workstations. Various hand-held, fixed-position and enclosure-type devices can also provide the beam emissions. Control of beam source 120 can be automated with the computer 104, or manual in the case of hand-held devices.

The sensor/receptor 122 can likewise be positioned internal or external to the patient. For example, various types of intraoral sensors are available. Phosphorus film sensors are used like X-ray film and are converted and "read" by the computer to transfer the digital data recorded thereon. Other types include charge coupled devices (CCD) and charged metal oxide semiconductor (CMOS) devices, which output digital data from respective circuits associated therewith. Micro printed circuits can be installed on such sensors and provide digital sensor output to the computer input 104a.

Still further, either or both of the beam source 120 and the sensor/receptor 122 can be preprogrammed for computer-controlled movement with respect to the patient 124. Thus, panoramic or tomographic images can be obtained with the patient immobilized. Such equipment is commercial available and typically moves through an arc of approximately 120 degrees for dental applications. The specific beam source 120 and sensor/receptor 122 components can be chosen as necessary for the type of model desired. For example, periapical, bite wing, full mouth, panoramic and cephalometric imaging are all widely used in dentistry, oral surgery and related fields. Still further, the system contemplates removable use on and inspection of individual tooth anatomy by use of a wand, pen or similar device adapted for placement intraorally by the dentist. Thus, the densitometry changes with respect to particular "watch" areas can be closely monitored.

Yet another type of beam source 120 comprises a miniaturized, hand-held CRT adapted for localized applications. For example, areas deemed susceptible to incipient caries and decay can be diagnosed and identified as "watch" areas, which the dental practitioner would specifically examine with such a miniaturized CRT source device during the course of follow-up office visits and procedures. Thus, patients would be exposed to only minimal levels of radiation in connection with such highly localized and tooth-specific densitometry models. An advantage of the system 102 is that models can be processed and compared nearly instantaneously. Thus, in a single appointment the dentist can obtain, compare and analyze multiple, limited-scope densitometry models specifically directed to areas of concern.

Figure 4A:
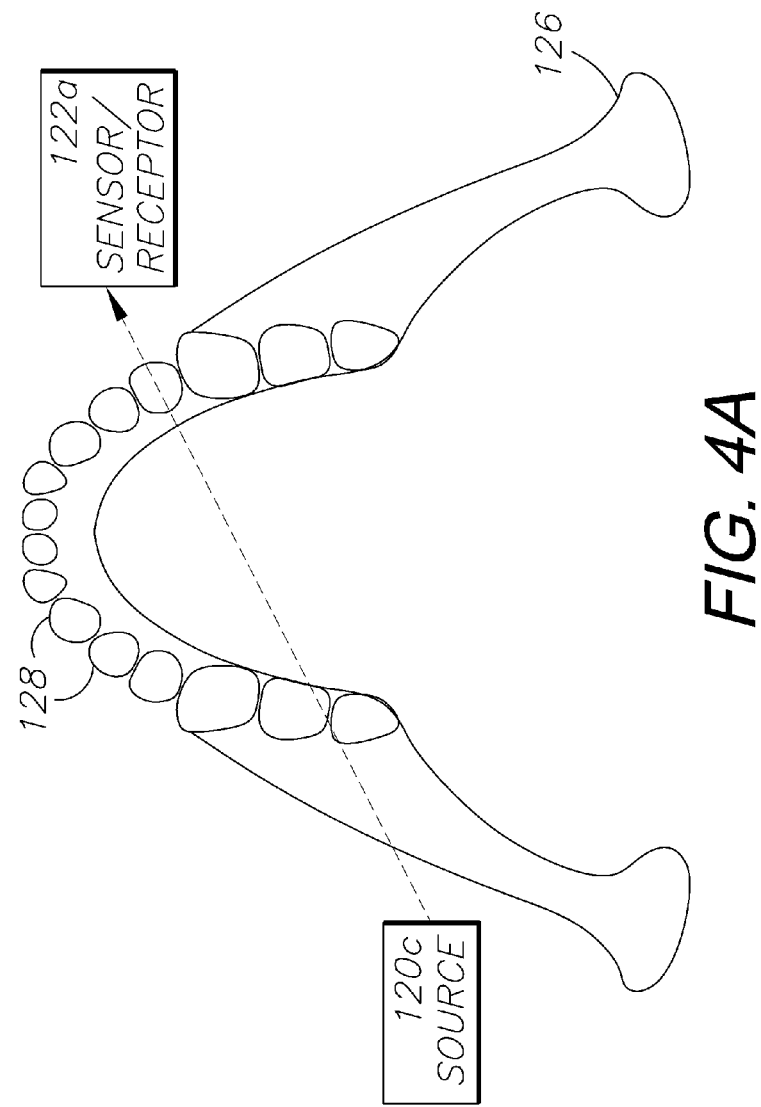
FIG. 4a is diagram of an application with an external beam source and an external sensor/receptor.
Figure 4B:
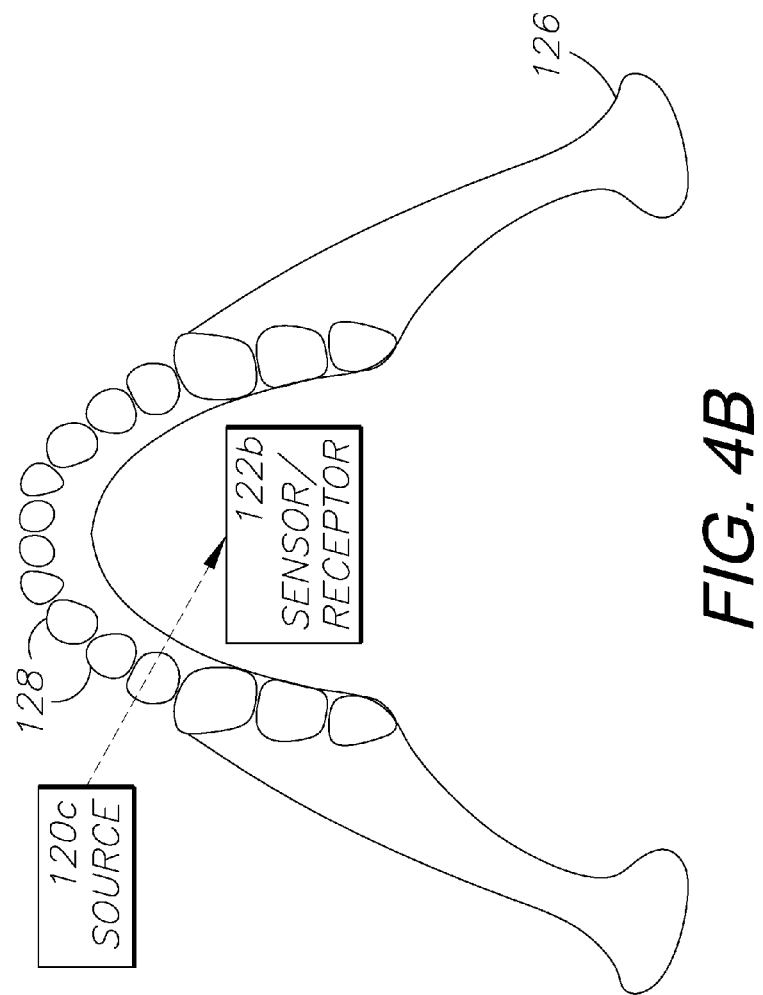
FIG. 4b is a diagram of an application with an external beam source and an internal sensor/receptor.
Figure 4C:
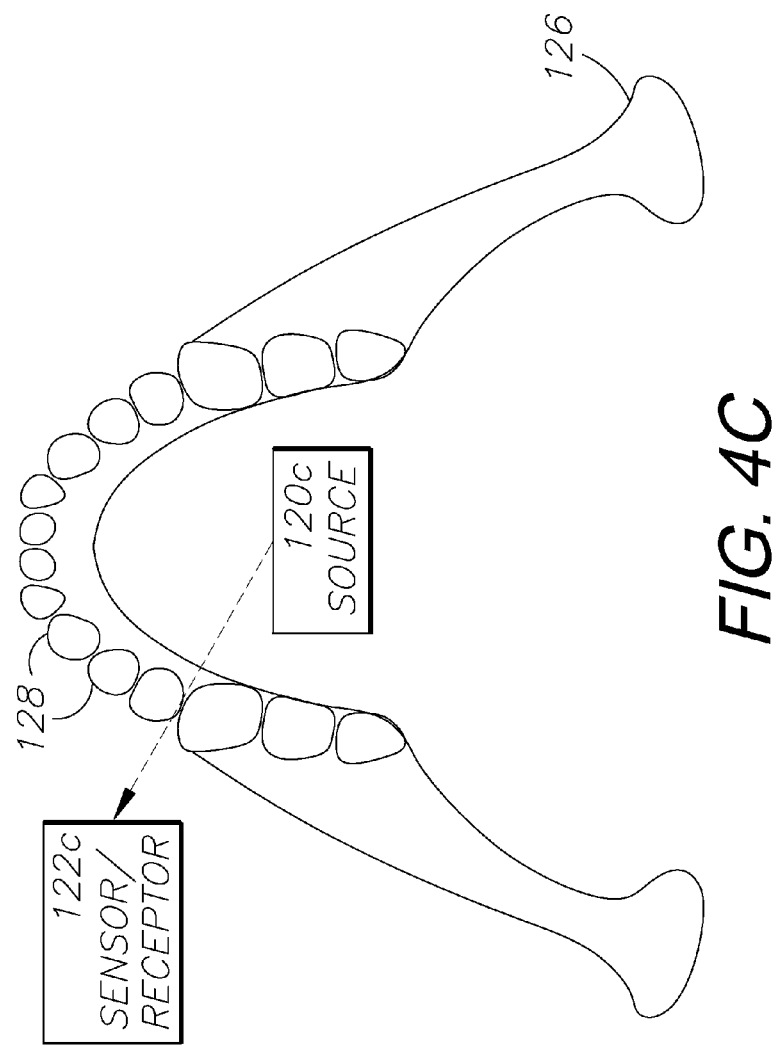
FIG. 4c is a diagram of an application with an internal beam source and an external sensor/receptor.

FIGS. 4a-d show alternative configurations and placements of the beam sources 120 and the sensor/receptors 122 with respect to the mandible 126 and teeth 128 of the patient 124. FIG. 4a shows a beam source 120a and a sensor/receptor 122a both placed externally whereby the beam passes through the patient 124. Such configurations can be preprogrammed to travel through predetermined arcs or orbits around the patient 124 in order to compile a panoramic, whole mouth or cephalometric image. FIG. 4b shows an external beam source 120b and an internal sensor/receptor 122b. FIG. 4c shows an internal beam source 120c and an external sensor/receptor 122c. FIG. 4d shows both the beam source 120d and the sensor/receptor 122d positioned intraorally.

V. Modified Densitometry Modeling Methods and Applications

Figure 5:
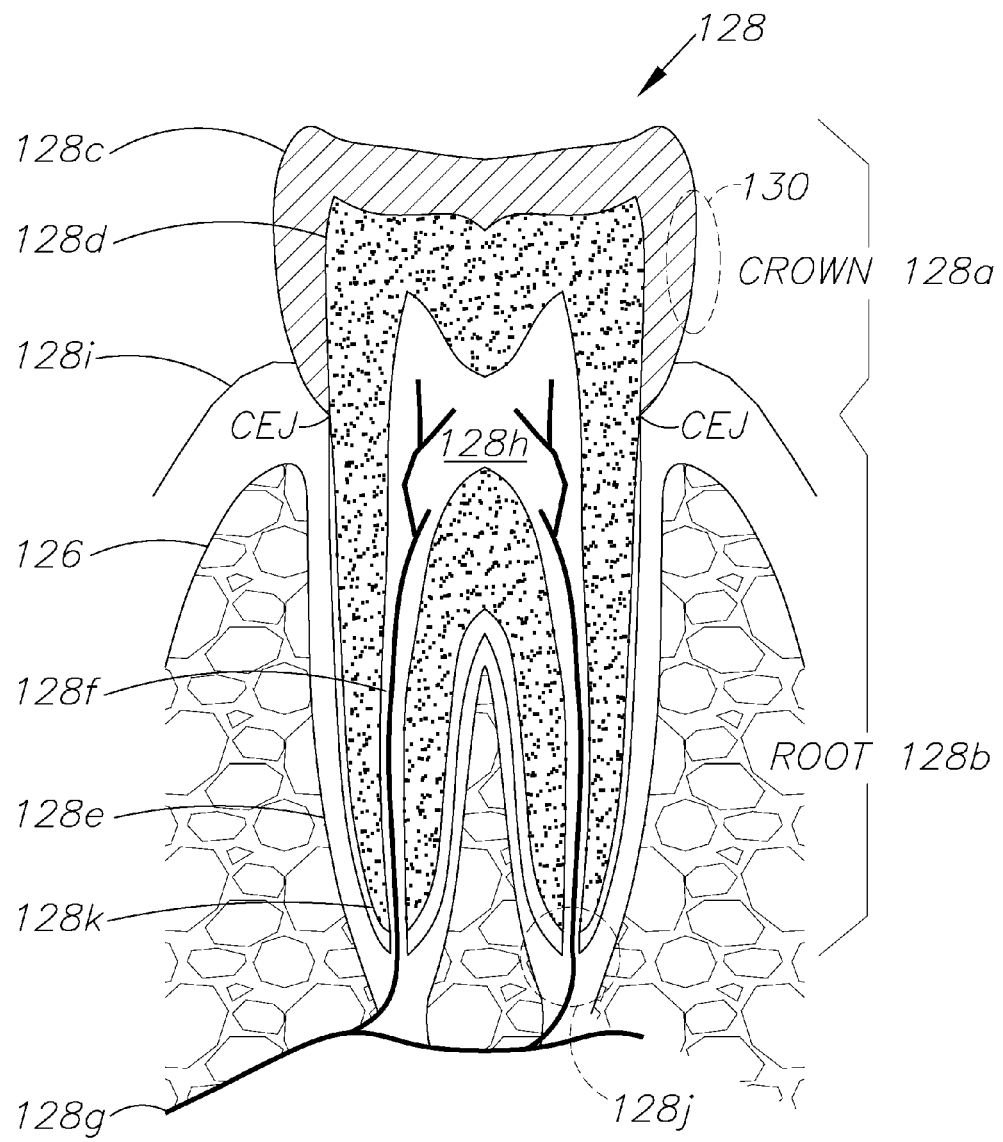
FIG. 5 is a diagram of a tooth structure, showing the locations of particular areas that are suited for densitometry monitoring with the system and method of the present invention.

Without limitation on the generality of useful dental and orthopedic applications of the modeling methods and applications for the present invention, several dental applications are described in detail. FIG. 5 shows a tooth 128 with a crown 128a and a root 128b. The crown 128a includes enamel 128c covering dentin 128d. The root 128b is embedded within a periodontal membrane 128e and includes a root canal 128f through which a neurovascular bundle 128g comprising a nerve, artery, vein and lymphatic components passes. The root canal 128f is filled with pulp 128h and surrounded by cementum 128k. The root 128b is embedded in the bone structure of the mandible or the maxilla 126, over which the gingiva and the gingival fibers 128i are located. The cementoenamel junction (CEJ) is located where the crown 128a meets the root 128b and is the common reference point for periodontal disease. Locations on the crown 128a between the adjacent teeth 130 are common locations for caries because bacteria tend to congregate in such locations unless dislodged by brushing and flossing. Another common problem area is located at the root apex 128j, where abscesses form.

Figure 6A:
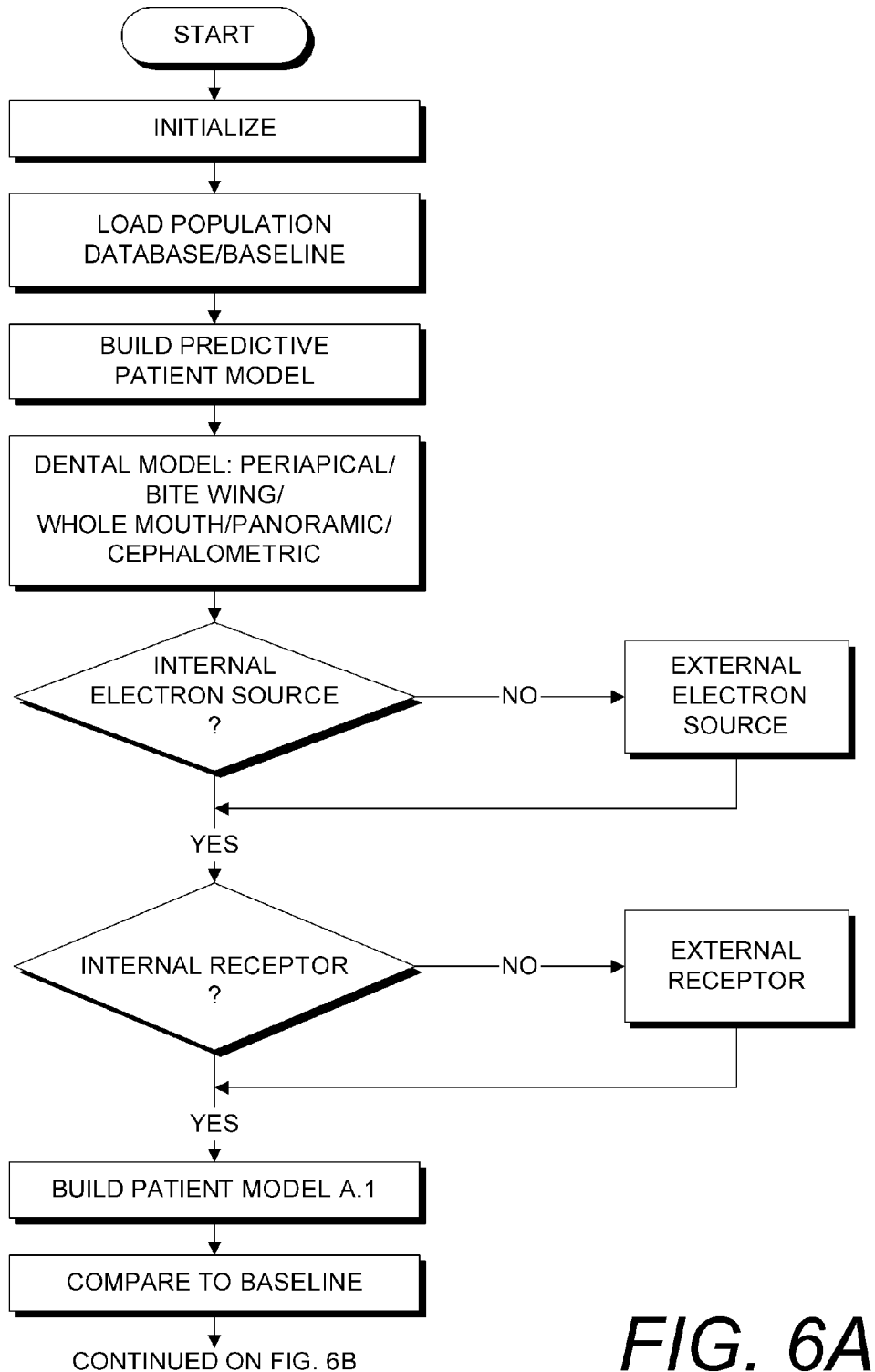
FIGS. 6a,b show a flowchart of a patient-specific densitometry modeling method according to the present invention.
Figure 6B:
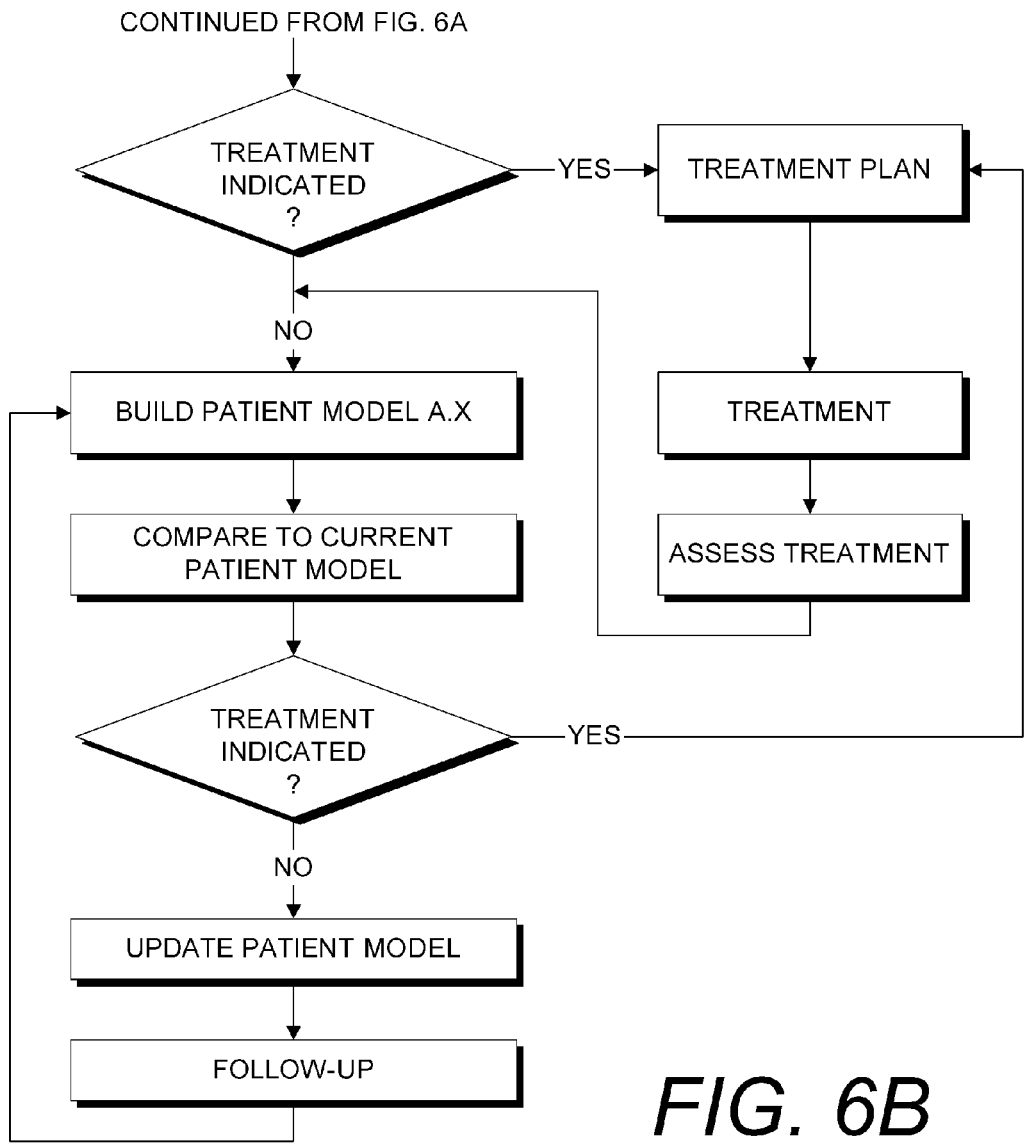

FIGS. 6a-b show a flowchart of the densitometry modeling method with respect to an individual patient. The steps of the flowchart generally correspond to routines, which can be performed either manually or with the computer 104. After starting and initializing the software, a population database/baseline is loaded. The population database/baseline can included densitometry data pertaining to the general population, or population subsets grouped by such variables and as age, gender, geographic area, etc. A predictive patient model is created from both population database information and patient-specific information, as discussed in more detail below. Examples of typical information used for creating dental models are shown, and include periapical, bite wing, whole mouth, panoramic and cephalometric densitometry data captures. Other types of data would be captured and used for creating patient models for other applications, such as orthopedic. Internal/external source/receptor selections (see FIGS. 4a-d) are made at the appropriate decision steps.

An initial patient model is created and can be compared to a corresponding baseline model for "normal" dental/orthopedic densitometries in individuals of corresponding age, gender and other variables. The initial model can be designated A.1. If indicated, treatment can be performed.

In a follow-up session, a second model A.X can be built. The variable "X" can correspond to, for example, the version number or a time period, such as the number of days since the first model A.1 was created. The software can perform a comparison between the two patient-specific models A.1 and A.X. Densitometry changes can be noted and brought to the attention of the dentist or physician. For example, areas showing significant decreases in densitometry would alert the dentist to the possibility of incipient caries. Depending on the extent of change and compromised density, preemptive treatment might be indicated, or the area can be designated for careful future monitoring for further deterioration or change. Because certain changes are normal, the baseline, plus the patient's dental/medical history, can be utilized in distinguishing conditions requiring treatment from normal decalcification/calcification.

Implant osseointegration can also be monitored with the system and methodology of the present invention. For example, the densitometry techniques described herein can monitor the progress of a bone-implant interface, indicating successful osseointegration, whereas the continued or increased presence of soft tissue granulation would indicate a failed implant.

Other conditions that are particularly well-suited for monitoring with the system and method of the present invention include fractures, decay, abscesses, plaque and periodontal disease. Still further, 3D imaging can be provided with the system and method whereby fractures and other lesions, which are difficult to detect in 2D imaging, can be made apparent.

Figure 7:
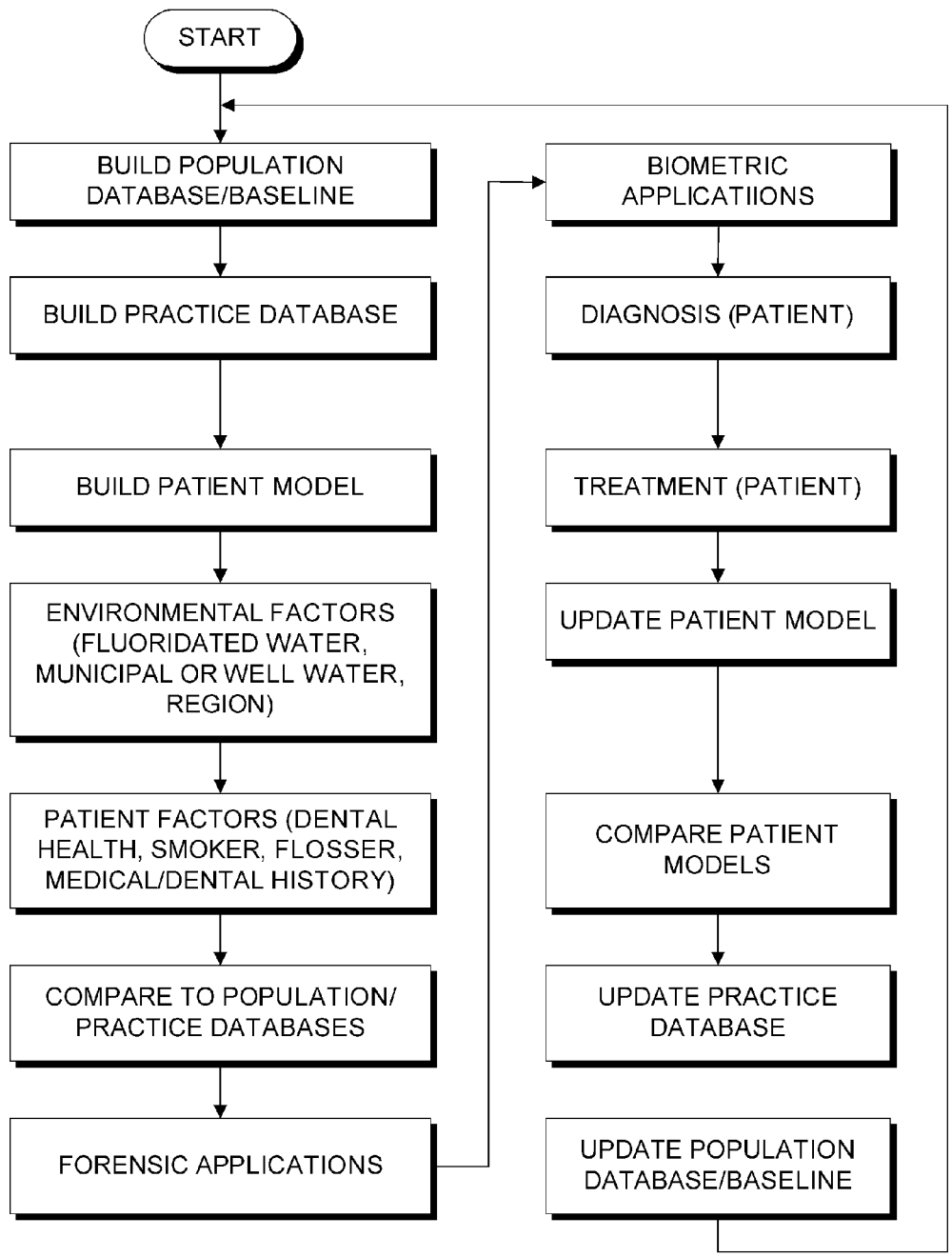
FIG. 7 is a flowchart of a general population baseline database densitometry modeling method according to the present invention.

FIG. 7 shows a flowchart for creating a baseline database, utilizing same in a dental or medical practice, and building individual patient densitometry models. As shown, the process is interactive with individual patient data being utilized in building the practice database, which in turn can be contributed to the general population baseline database. Thus, greater accuracy can be achieved in the baseline database over a period of time with contributed data from individual patients and practices. Still further, the individual patient model can be updated with each visit, and monitored against projected patient densities, as derived from the baseline.

Environmental factors, such as fluoridated, municipal or well water and geographic regional considerations can be applied as shown. Likewise, patient factors can influence the densitometry models. These include general dental health, dental hygiene (such as frequent and thorough brushing and flossing), systemic influences, oncology, zerostomia (dry mouth), transplant patients on anti-rejection medication, susceptibility to infection and decay, etc.

Additional embodiments and aspects of the method of the present invention include a number of additional applications of densitometry modeling, such as forensics, biometrics and individual identification. For example, individual identification from dental and medical records can be expedited by the digital data capture, processing, comparison and display techniques and procedures disclosed herein and adapted for use with densitometry models. In addition to the medical and dental applications, such procedures and the resulting models have applications in such fields as forensics, security (e.g., biometric identification techniques) and law enforcement.

VI. Digital Tomosynthesis Modeling/Imaging Systems, Methods and Applications

Figures 8A, 8B:
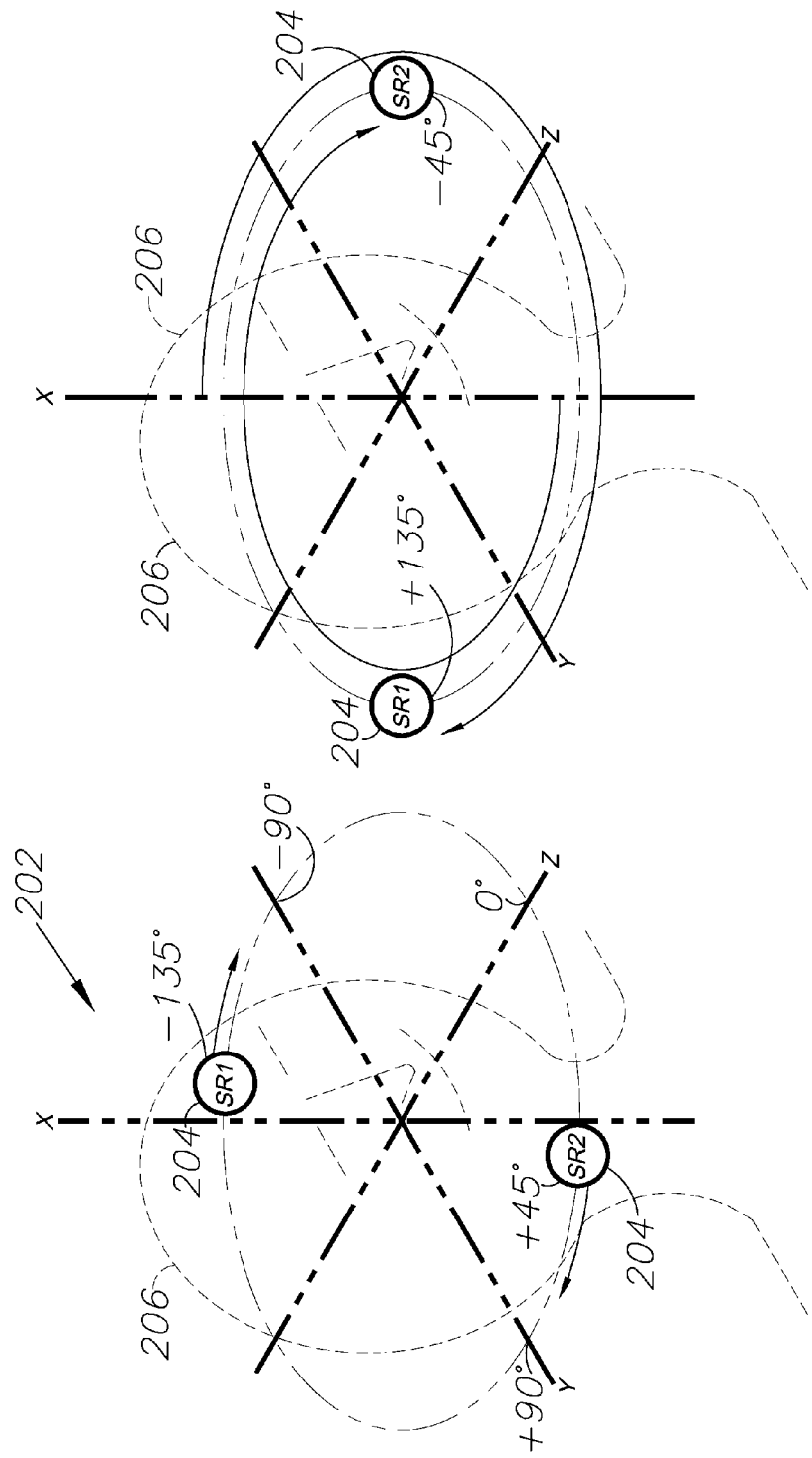
FIGS. 8A-D show an alternative embodiment of the invention comprising a pair of sensor/source units adapted for rotating around a patient in multiple planes defined by X, Y and Z axes.
Figure 8D:
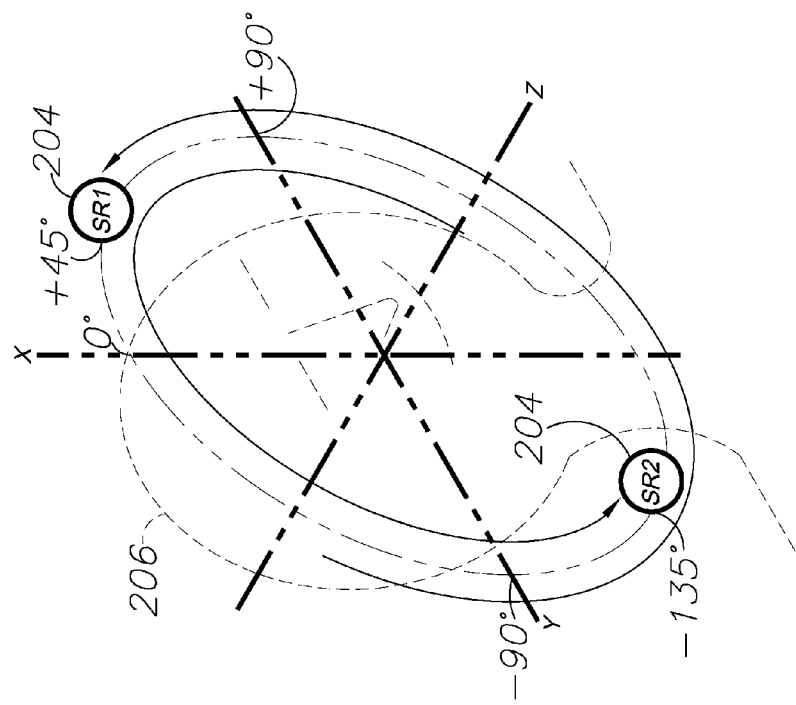
Figure 8C:
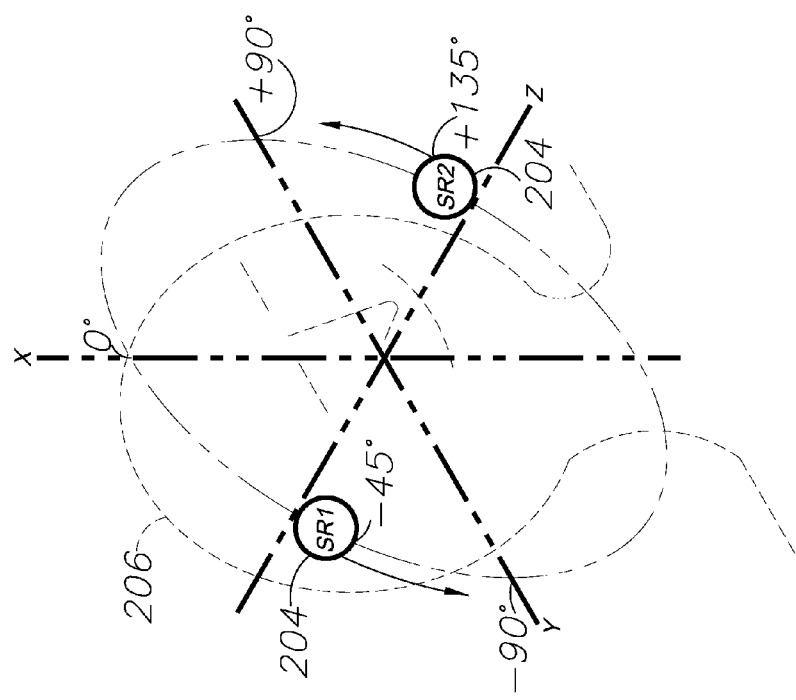

FIGS. 8A-D show a digital tomosynthesis radiographic densitometry modeling system 202 embodying another aspect of the invention and including a pair of combination source/receptor units 204 (SR1, SR2) each including a radiation source and a radiation receptor or sensor. The system 202 can utilize a variety of suitable modalities for capturing densitometry data. For example, dual energy x-ray absorptiometry (DEXA) uses low and high energy receptor sources and provides advantages for imaging and modeling, which are well-known in the field of dental imaging. The source/receptor units 204 are mounted on a suitable tracking device, which is adapted for revolving them around rotational axes corresponding to the position and orientation of a patient 206 relative to the system 202. As shown in FIGS. 8A-D, axes labeled X, Y and Z are defined relative to the head of a patient. Thus, the source/receptor units 204 rotate in a generally horizontal plane around the X axis (extending top-to-bottom) through approximately 270°. For example, SR1 rotates from a −135° (7:30 relative to a clock face) position (FIG. 8A) to a +135° (4:30 relative to a clock face) position (FIG. 8B) in either a clockwise (as shown) or a counterclockwise direction. The source/receptor units 204 operate to collect continuous densitometry signals using dual-energy techniques and components, which are well-known, whereby a first tomographic slice model is created. For dual energy x-ray absorptiometry (DEXA) modality operation, the source/receptor units 204 make two passes, each at a respective high/low energy level. A second planar tomographic slice model is created by rotating the source/receptor units 204 clockwise around the Z axis (extending anterior-to-posterior). For example, SR1 rotates from a −45° (10:30 clock face) starting position (FIG. 8C) clockwise to a +45° (1:30 clock face) ending position (FIG. 8D). Tomographic information can also be obtained by rotating the source/receptor units 204 around the Y axis (extending from side-to-side).

The resulting tomographic data are integrated and a 3-D image or model is calculated using this information. The extrapolation procedure includes the step of correcting and filtering the collected data in order to eliminate errors and distortion for a much higher degree of accuracy and comprehensiveness than would otherwise be possible with, for example, 2D computer modeling techniques. It will be appreciated that the tomographic slicing planes can be rotated or shifted axially as appropriate for modeling the region of interest (ROI). For example, the modeling procedure can be focused by locating the rotational centers of the source/receptor units 204 approximately on regions of interest (ROIs), with the entire 3-D digital tomosynthesis model being approximately centered thereon.

The applications of the modified system 202 include monitoring osseointegration of prostheses (i.e. orthopedic and dental) for diagnosing the effectiveness of prosthetic implant procedures and detecting potential problems and failures. Load-bearing prostheses can be regularly monitored for problems associated with loading whereby effective measures can be taken in a timely manner. Related problems can arise if the osseoprosthesis interface should become septic, which can lead to inflammation. In addition to radiographic sensing and modeling, thermographic data can be collected at specific areas of interest, such as prosthesis-tissue interfaces, and used to create graphic models which are useful for diagnosing and treating inflamed tissue conditions associated with septic conditions and other conditions causing inflammation, scarring and necrosis. The system 202 is also useful for 3-D morphology modeling of pulpal chambers and canals for endodontic applications.

Figure 9B:
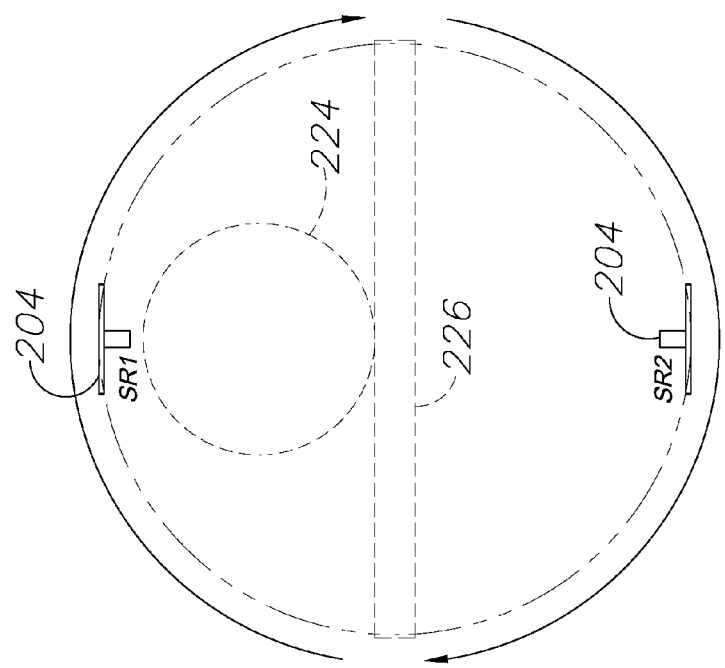
FIGS. 9A-B show another alternative embodiment of the invention comprising another pair of sensor/source units adapted for rotating around a patient or a patient body part.
Figure 9A:
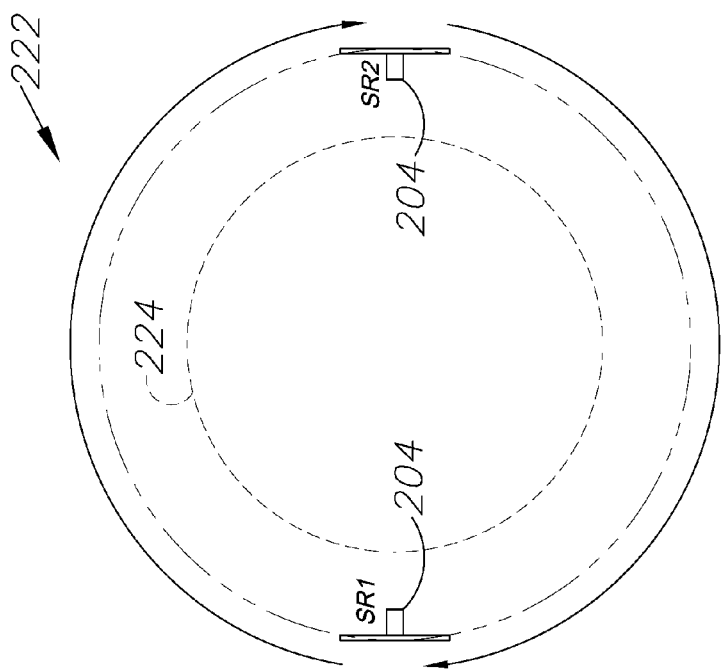

FIGS. 9A,B show another system 222 including source/receptor units 204 (SR1, SR2) mounted on suitable equipment for rotating through approximately 180° around a patient 224, e.g., a head, torso, limb, extremity, etc. As shown in FIG. 9B, a supporting structure 226, such as a table, can be provided for supporting the patient and the rotational apparatus in fixed relation.

FIGS. 10-12 show an application for digital tomosynthesis involving a hip prosthesis 232, which forms an area of osseointegration 234 with the femur 236. A path to be scanned 238 is defined along the length of the embedded shaft portion 240. Any of the various digital tomosynthesis techniques can be utilized for constructing the 3-D radiographic densitometry model, including those performed with the equipment and systems discussed above. FIG. 11 shows the resulting image from a filtering technique, which eliminates the signals corresponding to the osteal cement at the femur-prosthesis interface, and displays the femur bone structure only. FIG. 12 shows the reverse, with the osteal cement displayed in the resulting 3-D model. Such filtering techniques are well-known and call effectively eliminate scatter associated with fragments of bone, etc. Moreover, by controlling the filtering process various conditions can be detected, monitored, diagnosed and treated. For example, hairline fractures can be more easily detected using tomographic densitometry models than conventional x-rays.

Figure 14:
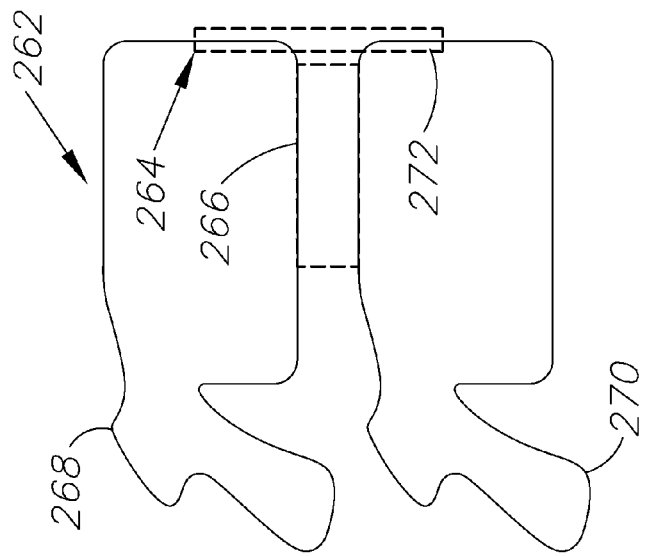
FIG. 14 shows an application of the invention in connection with invertebral fusion cages and plates.
Figure 13:
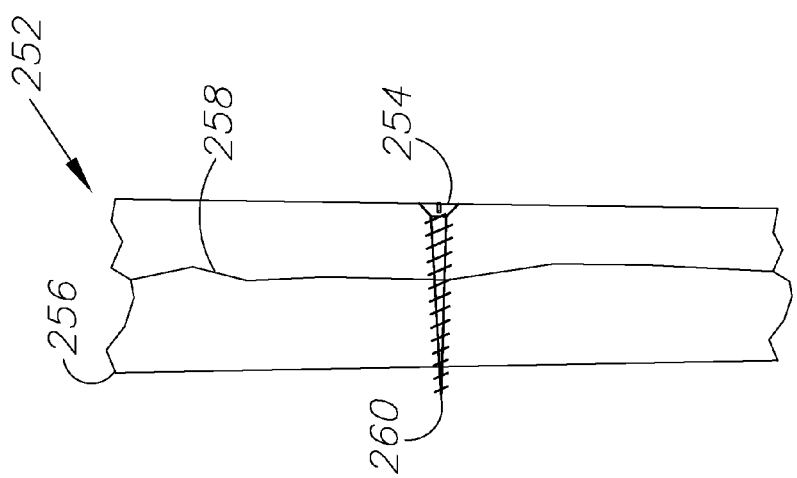
FIG. 13 shows an application of the invention in connection with detecting a bone screw protrusion.

FIG. 13 shows another application 252 involving a bone screw 254 extending through a bone 256 for closing a fracture 258. A tip 260 of the screw 254 protrudes from the surface of the bone 256, and could impede healing if not corrected. FIG. 14 shows another application 262 of the invention in connection with a spinal prosthesis, e.g. a vertebral cage structure 264 including a prosthetic disk portion 266 located between vertebrae 268, 270 and a vertebra-connecting plate 272. The present invention has utility in connection with spinal procedures whereby osseointegration, patient-prosthesis interfaces and various pathologies can be closely monitored. Close monitoring can be particularly important in spinal procedures because of the load-bearing conditions involved, and the significant effects on patient functionalities which are directly affected by such procedures and follow-up therapeutic and rehabilitation treatment.

Figure 15:
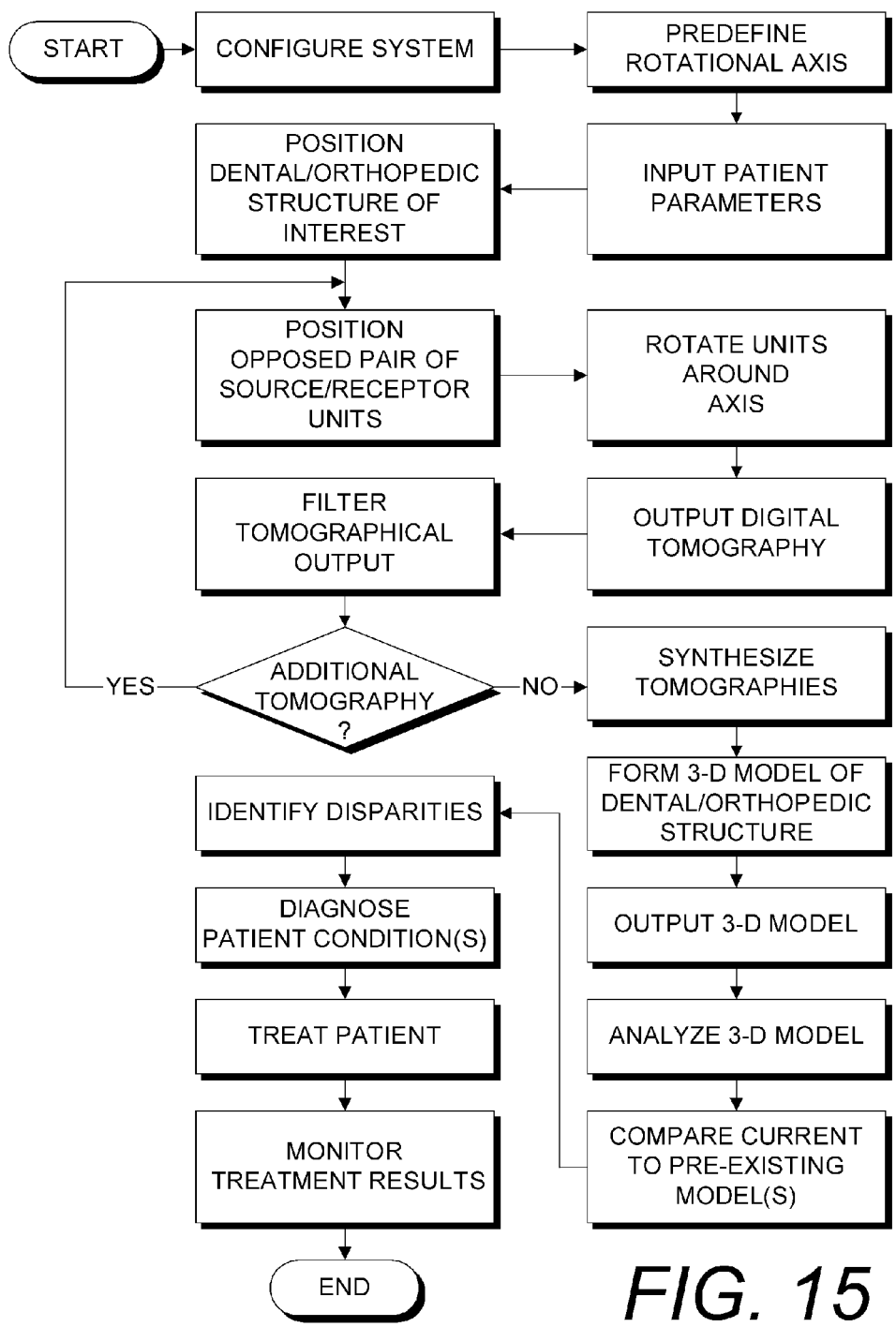
FIG. 15 is a flowchart for a digital tomosynthesis radiographic densitometry modeling method according to the present intention.

A flowchart of a method embodying an aspect of the present invention is shown in FIG. 15 and begins with configuring the system, e.g. preprogramming the controller according to various patient-specific parameters and other operating conditions, such as the rotational axes or paths of the source/receptor units 204. The patient region of interest (ROI) is positioned relative to the system. As described above, such patient positioning generally involves placing the patient ROI between a pair of source/receptor units 204. The system is programmed for rotating the units 204 around a first axis, and can also move the source/receptor units 204 axially, with radiographic densitometry information being output and filtered as necessary. In a DEXA operating mode, two passes (either rotary or axial) are made for each axis, one each at low and high energy levels in order to capture complete densitometry data corresponding to the different tissue types (i.e.

hard and soft tissues). Rotation around a second axis, and optionally around a third axis, can provide output in the form of additional radiographic densitometry information necessary to form a 3-D model by computer integration of the resulting signals, e.g., through a process such as digital tomosynthesis. The 3-D model can be output to a monitor, printer or other device, including a computer network or the Internet (worldwide web). The current 3-D model can optionally be compared to pre-existing models in order to detect changed conditions, which can be representative of either improving or worsening conditions. For example, disparities between such models formed at different times can indicate such changed conditions and can facilitate diagnosis. Treatment steps can next be implemented as appropriate and can be guided by the results of such modeling, analysis, comparison and diagnosis steps.

Figure 16:
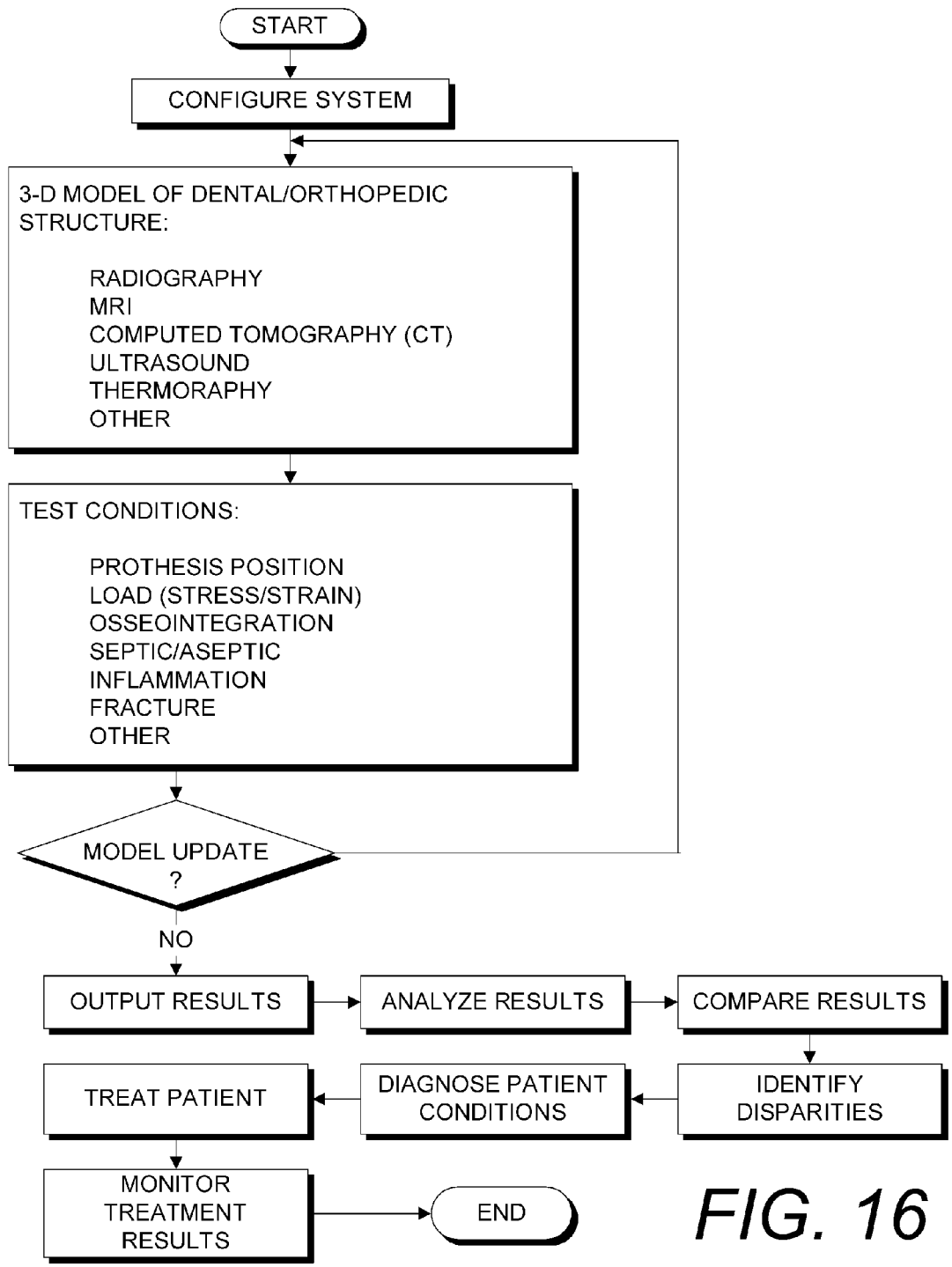
FIG. 16 is a flowchart for another medical/dental imaging/modeling method according to the present invention.
Figure 17:
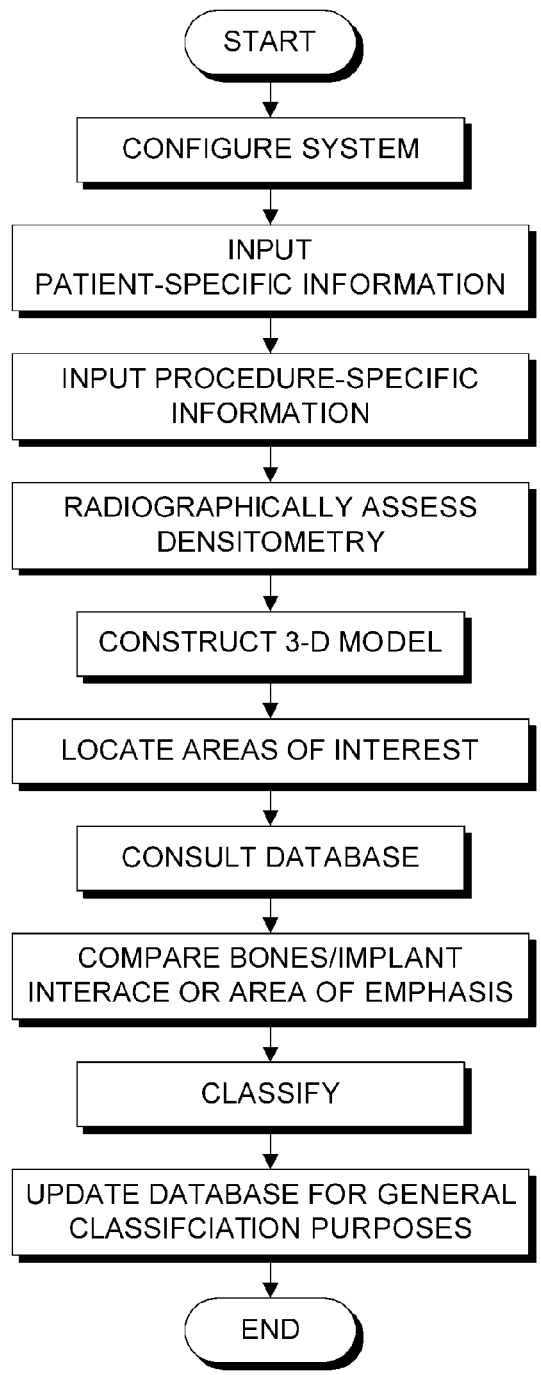
FIG. 17 is a flowchart showing a digital modality modeling method embodying an aspect of the present invention.

FIG. 16 shows another flowchart with an indication of the range of alternative steps and information sources applicable to the imaging and modeling methods disclosed herein. For example, the imaging technologies currently available include radiography, MRI, computed tomography (CT), ultrasound, fluoroscopy, sonar, Doppler effect, photon emission tomography (PET), single photon emission computed tomography (SPECT) scan and thermography. A variety of conditions can be tested for, including prosthesis position, load (i.e. stress and strain on the prosthesis or surrounding ROI), osseointegration, septic/aseptic conditions, inflammation, morphologies (e.g., pulpal chambers and canals for endodontics) in dentistry and fractures. The method shown in the flowchart of FIG. 16 can otherwise be similar to the methods discussed above.

It is to be understood that while certain aspects and embodiments of the invention are described and shown, the invention is not limited thereto and can assume a wide range of other, alternative aspects and embodiments.

What is claimed and desired to be secured by Letters Patent is as follows:

1. A 3-D digital medical and dental modeling system, which comprises:
   a computer including a digital memory adapted for storing patient densitometry information, at least one input, and at least one output;
   an input subsystem including a signal source and a signal receptor;
   a signal source positioning subsystem including a positioning motor and adapted for mounting said signal source and said signal receptor, said positioning subsystem connected to said computer and adapted for moving said source and/or said receptor through a predetermined path of movement relative to a patient;
   said receptor being connected to the computer input;
   said receptor producing signals to said computer input representing a condition of the patient's dental and/or orthopedic structure;
   said computer being adapted for creating, storing and comparing 3-D digital models of a patient's dental and/or orthopedic structure;
   an output device connected to said computer output and adapted for communicating condition information for said patient consisting of said 3-D digital model or relevant information for said patient derived from said model;
   said computer being adapted to access a general population baseline database of patient dental or orthopedic densitometry data including variables for age and gender, said computer also being adapted to create a plurality of baseline 3-D digital patient models created using said general population baseline database and said computer being further adapted for building a predictive, 3-D, digital general population, densitometry model for said patient based on information from said general population baseline database and from identified dental or orthopedic densitometry changes for said patient; and
   said computer being further adapted for performing automated digital comparisons of said identified dental or orthopedic densitometry changes for said patient with said predictive, 3-D, digital, general population, densitometry model for said patient.

2. The system according to claim 1 wherein said input subsystem includes:
   a pair of source/receptor units each including a signal source and a receptor;
   said signal positioning subsystem including a rotating mechanism mounting said source/receptor units in generally opposite relation with a patient region of interest (ROI) located therebetween; and
   said signal positioning subsystem being adapted for rotating said source/receptor units in both directions through coplanar, circular paths of movement around a first rotational axis.

3. The system according to claim 2, which includes:
   said signal source positioning subsystem including a second rotational axis defining a second set of coplanar, circular paths of movement of said source/receptor units; and
   said first rotational axis corresponding to an X axis extending top-to-bottom relative to the patient;
   said second rotational axis corresponding to a Z axis extending front-to-back relative to the patient; and
   said circular paths of movement having ranges of approximately between 90° and 270°.

4. The system according to claim 3, which includes:
   said input subsystem including a DEXA modality; and
   said signal source positioning subsystem rotating said source/receptor units in a first direction with said input subsystem at a low energy level and rotating said source/receptor units in a second direction with said input subsystem at a high energy level.

5. The system according to claim 2, which includes:
   said signal source positioning subsystem including an axial range of movement generally along a patient.

6. The system according to claim 2, which includes:
   a support structure for a patient located generally within a respective circular path of movement of said pair of source/receptor units.

7. The system according to claim 3 wherein said computer includes:
   a signal integration function for integrating signals obtained along said first and second paths of movement; and
   a 3-D modeling function for modeling a patient ROI in three dimensions from said integrated signals.

8. The system according to claim 1 wherein said computer includes:
   a filter function for filtering tomographic information from said receptor; and
   said filter function having a subtraction subfunction for subtracting signals corresponding to scatter and other extraneous information and a reversal subfunction for reversing the polarity and output of signals representing different types of structure.

9. The system according to claim 1 wherein said computer includes:

a digital processing function for constructing multiple slices at different depths and with different thicknesses from individual tomographic data acquisitions.

10. The system according to claim 1, which includes:
said input subsystem including a signal generating function chosen from among the group consisting of: digital tomosynthesis, dual energy x-ray absorptiometry (DEXA), radiography, magnetic resonance imaging (MRI), computed tomography (CT), ultrasound, photon emission tomography (PET), single photon emission computed tomography (SPECT) scan and thermography.

11. The system according to claim 1, which includes a function for assessing and modeling patient parameters chosen from among the group consisting of:
prosthesis position, load (stress/strain), osseointegration, septic/aseptic, inflammation and fracture.

12. A dental or orthopedic densitometry modeling method, which comprises the steps of:
providing an energy or field source;
providing a sensor for energy or a field emitted by said source;
providing a source/sensor positioning subsystem including a positioning motor and
connecting said positioning subsystem to said computer;
storing in said computer a predetermined path of movement of said positioning subsystem relative to the patient;
placing said source and sensor on opposite sides of the patient's dental or orthopedic structure to be modeled;
emitting energy or a field from said source, passing same through said patient's structure; and sensing said energy or field with said sensor;
guiding with said computer said source and sensor positioning subsystem through said predetermined path of movement;
building an initial patient-specific densitometry model;
obtaining current densitometry data on said patient;
performing with a computer time-lapse, automated digital comparisons of said initial and current patient-specific densitometry data, said comparisons identifying dental or orthopedic densitometry changes in the dental or orthopedic structures of individual patients;
identifying a localized dental or orthopedic structure area as a watch area based on densitometry model changes with respect to the patient;
directing said energy or field source towards the localized dental or orthopedic structure watch area; and
obtaining specific, localized densitometry information concerning the densitometry model of said area;
updating said initial patient-specific densitometry model;
providing as input to said computer a general population baseline database of patient dental or orthopedic densitometry data including variables for age and gender;
creating with said computer a predictive, 3-D , digital, general population, densitometry model;
performing with said computer automated digital comparisons of said identified dental or orthopedic densitometry changes with said general population baseline data; and
building a predictive densitometry model for a patient based on information from said database.

* * * * *